United States Patent [19]

Abramson et al.

[11] 4,311,652

[45] Jan. 19, 1982

[54] ARBUZOV REACTIONS EMPLOYING AN ALIPHATIC SOLVENT

[75] Inventors: Alan Abramson, White Plains; Edward D. Weil, Hastings-on-Hudson, both of N.Y.

[73] Assignee: Stauffer Chemical Company, Westport, Conn.

[21] Appl. No.: 154,170

[22] Filed: May 28, 1980

[51] Int. Cl.³ .................................................. C07F 9/40
[52] U.S. Cl. ..................................... 260/969; 260/990
[58] Field of Search ................................. 260/969, 990

[56] References Cited

U.S. PATENT DOCUMENTS

| | | | |
|---|---|---|---|
| 3,483,279 | 12/1969 | Davis et al. | 260/969 |
| 3,699,193 | 10/1972 | Melton | 260/969 |
| 3,776,984 | 12/1973 | Ratts | 260/969 |

*Primary Examiner*—Anton H. Sutto
*Attorney, Agent, or Firm*—Vivienne T. White

[57] ABSTRACT

An improved process for phosphite rearrangement wherein the phosphite is rearranged to the phosphonate. The improvement comprises conducting the phosphite rearrangement reaction in an aliphatic solvent which is miscible with the reactants at reaction temperatures, and immiscible with the product at lower temperatures. Increased yields of the phosphonate product are obtained without the need for additional distillation for solvent separation.

12 Claims, No Drawings

The advantage of conducting the rearrangement in a solvent were found to be a more easily controlled exotherm due to the heating and reflux of the solvent which removes the heat of reaction, and inhibiting the degradation of the phosphonate product produced. Solvents mentioned in the prior art as being suitable for use in such rearrangement reactions were those disclosed in U.S. Pat. No. 2,725,311.

The aromatic solvents utilized in the prior art have, however, required tedious distillation procedures to separate the solvent from the product. In prior art continuous rearrangement process using heat exchangers or stirred tanks, the product containing the solvent had to be immediately removed, and continuously distilled over a period of hours to remove the solvent. In the process of stripping the solvent additional product would be lost due to the formation of degradation products. A byproduct such as ethylene dichloride from the production of bis(2-chloroethyl) 2-chloroethylphosphonate, for instance, during the vacuum distillation process would deteriorate the vacuum, and cause the temperature to increase resulting in further product decomposition. This and other routes of decomposition, of 2-chloroethyl esters of phosphoric acids are disclosed by Kafengauz et al. in Soviet Plastics, April 1967, pp. 73–75 wherein the formation of 1,2-dichloroethane, vinyl chloride, acetaldehyde and acidic residual products are discussed. In addition to the distillation difficulties, even after distillation appreciable amounts of the prior art aromatic solvent would remain in the product.

U.S. Pat. No. 2,725,311 disclose the use of solvents in the preparation of the phosphonate product by a process in which phosphorus trihalide is reacted with alkylene oxide and the temperature is raised to 150° C. to cause the rearrangement. Suitable solvents were disclosed to be o-dichlorobenzene, aromatic mineral spirits, ethanol, or those solvents capable of dissolving the phosphonate which are easily volatized.

U.S. Pat. No. 4,144,387 discloses the slow addition of tris(2-chloroethyl) phosphite to a product heel (i.e, a heel of the preformed product) at a temperature below 180° C. to avoid side reactions such as polymerization. The initial heel is said to be produced by the autogenous reaction of the phosphite at 175° C. over a period of hours using o-dichlorobenzene as the solvent. After the initial heel was produced it was used in the subsequent production process to form additional phosphonate product without any additional solvent. This method is said to eliminate the need for using the inert solvent in the final product run, which would necessitate expensive solvent separation.

The object of the invention disclosed herein is to provide a means whereby the thermal isomerization of the phosphite can be accomplished to form the phosphonate product, without the necessity of further distillation to remove the solvent.

Another object of the invention is the production of high quality bis(2-chloroethyl) 2-chloroethyl phosphonate by the rearrangement of tris(2-chloroethyl) phosphite using a solvent which can be conveniently and economically removed from the product.

Other objects of the invention or advantages of the invention will be evident from the following disclosure.

SUMMARY OF THE INVENTION

The invention is a novel process for performing the Michaelis-Arbuzov or Arbuzov rearrangement, desirably a haloalkyl phosphite, and in particular, it is a novel process for rearranging tris(2-chloroethyl) phosphite. The invention is directed to phosphite rearrangements, wherein the novel process comprises conducting the rearrangement process in an essentially aliphatic solvent which is miscible with the reactants at the reaction temperature, but substantially immiscible with the phosphonate product at lower temperatures. One advantage of the novel process is the simple and economical separation of the product from the solvent as by phase separation in contrast with the prior art process which required tedious and expensive distillative separation.

DETAILED DESCRIPTION OF THE INVENTION

The invention process disclosed herein is directed to the rearrangement of a phosphite to produce a phosphonate. The invention is also desirably directed to the rearrangement of tris(2-chloroethyl) phosphite to form bis(2-chloroethyl) 2-chloroethyl phosphonate.

The process of the invention comprises conducting the rearrangement process in an essentially aliphatic solvent which is miscible with the reactant or reactants at the reaction temperature but substantially immiscible with the product at lower temperatures.

The term "essentially aliphatic" is used herein to mean solvents which are comprised primarily of aliphatic moieties as opposed to aromatic components. Use of the term "substantially immiscible" means that only small amounts of the phosphonate product are soluble in the solvent at room temperature.

The variation in solubility of the reactants and product with temperature, allows the solvent to be removed by a simple phase separation. The disclosed process is therefore more convenient, and more economical than the distillation separation which would normally be required when using solvents disclosed in the prior art.

The intramolecular rearrangement of the phosphite to form the phosphonate product using the solvents disclosed herein is applicable to known batch or continuous production methods.

Solvents suitable for use in the novel process disclosed herein are aliphatic and preferably alkane solvents such as hexanes, heptanes, octanes, nonanes, decanes, dodecanes, tetradecanes, eicosanes and mixed alkanes as Soltrol ®170, which is a Phillips Petroleum Company brand of a mixed aliphatic hydrocarbon solvent. The selection of alkanes boiling above 140° C. permits the use of atmospheric pressure or high pressure.

The use of solvents which are mixtures of aromatic and aliphatic hydrocarbon are also within the scope of the invention if they are predominantly aliphatic and meet the criteria of being miscible with the reactant or the reactants at the reaction temperature and are essentially or substantially immiscible with the phosphonate product at lower temperatures. Ashland Chemical Company's low odor base solvent (primarily comprised of isoparafin hydrocarbons with about 4% aromatics and traces of olefin) is a suitable solvent for use in the process.

Solubility tests conducted on tris(2-chloroethyl) phosphite and bis(2-chloroethyl) 2-chloroethylphosphonate at room temperatures showed that both were soluble in aromatic solvents. Similar solubility tests indicated that heptane is a poor solvent for both the phosphite ester and the phosphonate product at ambient temperatures, but on warming to about 70° C. the phosphite was found to be very soluble whereas the phos-

ARBUZOV REACTIONS EMPLOYING AN ALIPHATIC SOLVENT

BACKGROUND OF THE INVENTION

1. Field of the Invention

The present invention relates to a novel method of carrying out Michaelis-Arbuzov or Arbuzov type rearrangements, and more particularly, it relates to the autogeneous rearrangement of tris(2-chloroethyl) phosphite to bis(2-chloroethyl) 2-chloroethylphosphonate.

2. Prior Art

Michaelis-Arbuzov reactions have long been known, having been first described in J. Russ. Phys. Chem. Soc. Vol. 38, 687 (1906). As a result of extensive investigations in the field it has come to be accepted that the Michaelis-Arbuzov reaction in its simplest form comprises the reaction with rearrangement of a phosphite with an organic halide, to obtain a phosphonate. An illustrated equation is as follows:

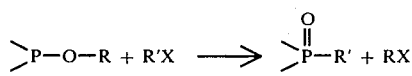

wherein R is an alkyl or substituted alkyl radical, X is halogen and R' is an alkyl or substituted alkyl having at its point of attachment to X an aliphatic carbon atom.

If R and R' are identical only catalytic quantities of R'X are required to cause rearrangement of the phosphite to phosphonate. On the other hand, where R and R' are different, a stoichiometric amount of R'X is required to prepare the desired phosphonate product. In each case the rearrangement is accomplished by heating.

In certain instances, however, where an ester group of the phosphite reactant itself bears a halogen atom bonded to an aliphatic carbon atom as, for instance, a tris(2-chloroethyl) phosphite, the presence of any separate organic halide reactant is unnecessary. The reaction illustrated below is frequently spoken of as the Arbuzov rearrangement and constitutes a specialized embodiment of the generic Michaelis-Arbuzov reaction:

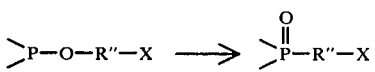

where R" is an alkyl or substituted alkyl having at its point of an attachment to X an aliphatic carbon atom.

The scope of reactants available for the reaction has been defined in the course of the investigation carried out since 1906. It has come to be known that all that is critical to the reaction is:

(1) that the phosphite reactants embody a trivalent phosphorus atom that carries an ester group, therefore:

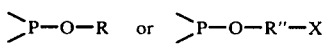

and, that the R' group of a separate organic halide reactant or the R" group where the phosphite itself contains reactive halogen have at its point of attachment to the halogen an aliphatic carbon atom; in addition, in the instance of R", it is critical that the halogen (X) be attached to a carbon atom which is a beta carbon with respect to the oxygen moiety, or to a carbon atom which is further removed from the oxygen moiety. The moieties other than those illustrated above do not participate in this reaction and hence their identity is not critical.

For example, reaction goes forward with phosphite esters:

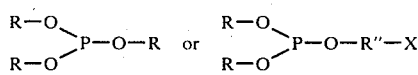

with phosphonite esters:

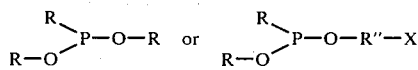

with the phosphinite esters:

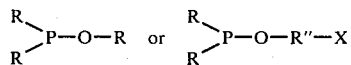

or expressed more generically, with any compound of the formula:

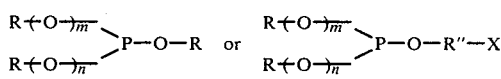

where each R, taken separately, independently represents hydrocarbon or substituted hydrocarbon, or two R groups, taken jointly, together represents a divalent radical which with the phosphorus atom represents a cyclic unit, and each of m and n independently is an integer from 0 to 1. In the instance of phosphite and phosphonite esters wherein not all oxygen containing moieties are the same, mixtures of products will result. Not withstanding, the reaction goes forward and the resulting mixtures are conventionally separated.

It is necessary to control the process temperature and the residence time especially at high reaction temperatures to inhibit a degradation of the product. As a result, prior art batch processes generally necessitated a low reaction temperature over a long reaction time to avoid side reactions.

Prior art methods of carrying out the reaction are, for instance, by passing a thin film of liquid reaction mixture (to provide close temperature control) through a reaction zone at a temperature of 195° C. to 260° C. as illustrated in U.S. Pat. No. 3,483,279 to Davis et al., or by heating of the phosphite in a reactor at about 160° C. for five hours with or without the use of a solvent. The latter method, however, has been found to be of low efficiency and very slow and is usually carried out in a batch-wise operation. The latter method utilizing a solvent requires further distillation in order to separate the product from the solvent used.

Tris(2-chloroethyl) phosphite is known to undergo a molecular rearrangement to form bis(2-chloroethyl) 2-chloroethylphosphonate at temperatures in the range of about 150°-180° C. Historically, the use of a reaction solvent has resulted in better yields than if no solvent is used.

phonate was only slightly soluble. It was found that with increasing carbon number alkanes the solvent power decreased slightly for the phosphite and phosphonate tested.

The choice of a suitable solvent in the practice of the invention will be dependent, therefore on its miscibility or immiscibility within the applicable temperature range with the reactant and the phosphonate product.

In accordance with the disclosed invention, the solvent is heated in a reactor close to or at its initial boiling point, which should correspond to the desired reaction temperature for the rearrangement of the phosphite to the phosphonate. It is of course understood that rearrangement reactions using solvents having boiling points below the desired reaction temperature range can be conducted under pressure to raise the boiling temperature of the low boiling solvents. The reactant or reactants are then charged to the reactor over a period of time and held at the reaction temperature to insure rearrangement of a substantial amount of the phosphonate.

Although it is preferred to charge the reactant slowly to the solvent at the reactor temperature (the boiling point) to more easily control the exothermic reaction, it is also within the scope of the invention to mix the solvent and reactant at room temperature and then slowly heat the mixture to the reflux temperature.

Precaution should be taken to avoid build-up of unreacted phosphite at high temperatures which could suddenly react. Addition rates should be adjusted to match the reaction rate at the temperature used. Temperatures for the rearrangement of tris(2-chloroethyl) phosphite of from about 140°-300° C. are desirable although, temperatures of from 180°-220° C. are preferred.

It is advantageous in the practice of the invention, especially in a higher temperature reaction process to utilize varying ratios of solvent to reactant to increase or decrease the temperature at which the solvent initially separates from the product (kick out temperature). Generally, a 1:1 ratio of solvent to reactant is used in the rearrangement process. It was found, however, that if less solvent than reactant is used, the "kick out" temperature will be higher and conversely more solvent than reactant lowers the "kick out" temperature.

An important advantage realized by practicing the novel process disclosed herein is that by utilizing a disclosed solvent and adjusting the temperature, and the solvent to reactant ratio, a process can be achieved wherein a product-rich phase will separate from the solvent-rich phase at reaction temperatures. Thus, as the phosphonate product is formed, it separates, and can be removed. This is especially advantageous for a continuous rearrangement process since a product-rich phase can be continuously, easily and economically removed during reaction. The product-rich phase contains a greatly reduced solvent to product ratio which can be separated by phase separation at near ambient temperatures. The solvent then being recycled.

It is also within the scope of the invention to use a disclosed solvent which will separate from the phosphonate product (the solvent being a poor solvent for the product at the reaction temperature) at the reaction temperature without the need for varying the solvent to reactant ratio. As in the above, the product-rich phase will separate from the solvent rich phase at reaction temperatures and can be separated as disclosed above.

In any event in any production process in accordance with the disclosed invention, the solvent and the rearranged product upon cooling become immiscible and the product is removed by phase separation leaving the solvent within the reactor.

The solvent used in the manner disclosed above is, of course, recoverable and reusable, especially if the reactor overhead system is arranged to minimize solvent loss through venting to the atmosphere. It is desirable to utilize a solvent recovery system as for instance, a partial condenser which will condense the solvent while removing low boiling degradation products. Alternatively, the solvent can be purified in a stripping process.

The yield of the phosphonate product by the isomerization of the phosphite in the following examples could not be accurately assessed by direct NMR or wet analysis due to the presence of polymeric by-products which mimicked the product response. The yield was, therefore, determined by converting the phosphonate product to bis(2-chloroethyl) vinyl phosphonate by dehydrohalogenation using the method disclosed in Example II of U.S. Pat. No. 3,548,040. The dehydrohalogenation process is known to result in some loss of the phosphonate product through decomposition generally in the range of 3–8%.

The following results clearly show the advantage of the disclosed process over the prior art continuous rearrangement process in which the yield of vinyl phosphonate after dehydrohalogenation is generally about 55%.

EXAMPLE I

Tris(2-chloroethyl) phosphite having a purity of about 91% was rearranged to bis(2-chloroethyl) 2-chloroethylphosphonate using Soltrol 170 ® as the reaction solvent. In the process 1602.7 grams of Soltrol 170 ® were heated in a 1 liter 3-neck flask to a temperature of from 202°-205° C. and 1601.1 grams of tris(2-chloroethyl) phosphite were slowly added over a period of 1½ hours. The mixture was maintained at a temperature of from 214°-203.5° C. for another hour then slowly cooled to room temperature and separated by phase separation. The "kick out" temperature was about 192° C. The weight of the product layer after phase separation was 1569.2 grams and the weight of the solvent layer was 1626.1 grams.

The conversion of the phosphite was about 96%. The yield of bis(2-chloroethyl) vinyl phosphonate was 72.0%.

EXAMPLE II

The rearrangement of tris(2-chloroethyl) phosphite was conducted in an N-dodecane solvent using the same equipment as disclosed in Example I. In the process 156.9 grams of the solvent were mixed with 149.1 grams of the phosphite at room temperature and then charged to the reaction flask. The mixture was slowly heated to 214° C. and refluxed for 1¾ hours at between 214° C. and 199.5° C., and then cooled to room temperature. The "kick out" temperature (solvent separation initiated) was about 196° C. The solvent layer was separated from the product layer by simple phase separation. The weight of the product layer after phase separation was 143.4 grams and the solvent layer weighed 157.4 grams.

The percent conversion of the phosphite was about 96%. The yield of bis(2-chloroethyl) vinyl phosphonate was about 72%.

The bis(2-chloroethyl) 2-chloroethyl phosphonate is useful as a flame retardant, and as an intermediate for the production of bis(2-chloroethyl)vinylphosphonate (a monomer), and as an intermediate for the production of 2-chloroethylphosphonic acid, a plant growth regulator.

What is claimed is:

1. A novel process for the rearrangement of a phosphite to the phosphonate product comprising conducting the rearrangement process in an essentially aliphatic solvent which is miscible with the reactants at the reaction temperature, but substantially immiscible with the phosphonate product at lower temperatures.

2. The process of claim 1 wherein the phosphite is a haloalkyl phosphite.

3. The process of claim 1 wherein the phosphite is tris(2-chloroethyl) phosphite.

4. The process of claim 1 wherein the solvent is an alkane.

5. The process of claim 1 wherein the solvent is essentially aliphatic having some aromatic components.

6. The process of claim 1 wherein the solvent is a mix aliphatic solvent having a boiling temperature within the range of 180°–220° C.

7. The process of claim 1 wherein the solvent is dodecane.

8. The process of claim 1 wherein the solvent is a low odor base solvent.

9. The process of claim 1 wherein the solvent to phosphite ratio is 1:1.

10. The process of claim 1 wherein the solvent to phosphite ratio is less than 1:1.

11. The process of claim 1 wherein the solvent to phosphite ratio is greater than 1:1.

12. The novel process of claim 1 wherein the process is continuous.

* * * * *